(12) United States Patent
Herceg et al.

(10) Patent No.: US 12,138,018 B2
(45) Date of Patent: Nov. 12, 2024

(54) EYEWEAR DEVICE

(71) Applicant: Nokia Technologies Oy, Espoo (FI)

(72) Inventors: Marijan Herceg, Osijek (HR);
Tomislav Matic, Osijek (HR)

(73) Assignee: Nokia Technologies Oy, Espoo (FI)

( * ) Notice: Subject to any disclaimer, the term of this patent is extended or adjusted under 35 U.S.C. 154(b) by 293 days.

(21) Appl. No.: 17/020,260

(22) Filed: Sep. 14, 2020

(65) Prior Publication Data

US 2021/0076948 A1 Mar. 18, 2021

(30) Foreign Application Priority Data

Sep. 16, 2019 (EP) .................................... 19197433

(51) Int. Cl.
*A61B 5/0205* (2006.01)
*A61B 5/00* (2006.01)
*A61B 5/11* (2006.01)

(52) U.S. Cl.
CPC .............. *A61B 5/0205* (2013.01); *A61B 5/11* (2013.01); *A61B 5/6803* (2013.01); *A61B 5/0004* (2013.01); *A61B 2562/0214* (2013.01)

(58) Field of Classification Search
None
See application file for complete search history.

(56) References Cited

U.S. PATENT DOCUMENTS

| | | | | |
|---|---|---|---|---|
| 3,602,222 | A | * | 8/1971 | Herndon ................ A61B 5/352 324/76.39 |
| 9,486,156 | B2 | | 11/2016 | Kato et al. |
| 9,955,895 | B2 | | 5/2018 | Jin et al. |

(Continued)

FOREIGN PATENT DOCUMENTS

| CN | 107743605 A | 2/2018 |
|---|---|---|
| CN | 109856815 A | 6/2019 |

(Continued)

OTHER PUBLICATIONS

Graybill et al., "Eyelid Drive System: An Assistive Technology Employing Inductive Sensing of Eyelid Movement", IEEE Transactions on Biomedical Circuits and Systems, vol. 13, No. 1, Feb. 2019, pp. 203-213.

(Continued)

*Primary Examiner* — Rene T Towa
*Assistant Examiner* — Aurelie H Tu
(74) *Attorney, Agent, or Firm* — Harrington & Smith

(57) ABSTRACT

An apparatus, method and computer program is described comprising: applying an electrical signal to a first electrical circuit formed between a first device electrode and a first eyelid electrode, an eyeball electrical path between the first eyelid electrode and a second eyelid electrode, the second eyelid electrode and a second device electrode, and the second device electrode and the first device electrode; and determining current and/or voltage measurements of the first electrical circuit, wherein a current and/or voltage is generated in the first electrical circuit in response to the applied electrical signal, and wherein the first device electrode is configured to form a first capacitor with the first eyelid electrode and the second device electrode is configured to form a second capacitor with the second eyelid electrode.

16 Claims, 9 Drawing Sheets

(56) References Cited

U.S. PATENT DOCUMENTS

| | | | | |
|---|---|---|---|---|
| 2007/0010748 | A1* | 1/2007 | Rauch | G16H 40/67 600/481 |
| 2009/0281394 | A1* | 11/2009 | Russell | A61B 5/0002 600/301 |
| 2010/0240982 | A1* | 9/2010 | Westbrook | A61B 5/4818 600/538 |
| 2014/0148656 | A1* | 5/2014 | Zielinski | A61B 5/0537 600/301 |
| 2014/0192312 | A1 | 7/2014 | Pletcher et al. | |
| 2015/0335288 | A1* | 11/2015 | Toth | A61B 5/6833 600/391 |
| 2016/0225244 | A1* | 8/2016 | Gui | A61B 5/1126 |
| 2016/0256086 | A1 | 9/2016 | Byrd et al. | |
| 2017/0042432 | A1* | 2/2017 | Adib | G01S 13/536 |
| 2017/0049395 | A1* | 2/2017 | Cao | A61B 5/6821 |
| 2017/0105660 | A1 | 4/2017 | Landau et al. | |
| 2018/0173011 | A1 | 6/2018 | Barrows et al. | 7/83 |

FOREIGN PATENT DOCUMENTS

| | | |
|---|---|---|
| DE | 102015000248 A1 | 7/2016 |
| EP | 3338623 A1 | 6/2018 |
| JP | 2004254876 A | 9/2004 |
| JP | 2009273861 A | 11/2009 |
| JP | 2015205114 A | 11/2015 |
| KR | 20160031756 A | 3/2016 |
| WO | WO-93/02616 A1 | 2/1993 |
| WO | 2013/110846 A1 | 8/2013 |
| WO | 2017/058402 A1 | 4/2017 |

OTHER PUBLICATIONS

Lee et al., "Non-Contact Blink Detection Glasses Utilising Transparent Conductive Film for Binary Communication", Electronics Letters, vol. 51, No. 5, Mar. 5, 2015, pp. 382-384.

"Transparent Electrodes", Sefar, Retrieved on Jul. 21, 2020, Webpage available at : https://www.sefar.com/en/609/Transparent-Electrodes.htm?Product=3540276.

Sakamoto et al., "Highly Flexible Transparent Electrodes Based on Mesh-Patterned Rigid Indium Tin Oxide", Scientific Reports, vol. 8, No. 2825, 2018, pp. 1-8.

Kim al.. "A Highly Flexible Transparent Conductive Electrode Based on Nanomaterials". NPG Asia Materials. vol. 9, 2017, pp. 1-9.

"Medical Electrodes and Biosensor Conductive Inks", Tekra, Retrieved on Jul. 21, 2020, Webpage available at : https://www.tekra.com/products/conductive-inks/medical-electrodes-and-biosensor-conductive-inks.

"Electric Conductive Ink for Printed Electronics" Nagase America LLC, Retrieved on Jul. 21, 2020, Webpage available at : https://nagaseamerica.com/product/electric-conductive-ink-printed-electronics/.

Zhang et al., "Simultaneous Detection of Blink and Heart Rate using Multi-channel ICA from Smart Phone Videos", Biomedical Signal Processing and Control, vol. 33, Mar. 2017, pp. 189-200.

Tag et al., "Continuous Alertness Assessments: Using EOG Glasses to Unobtrusively Monitor Fatigue Levels In-The-Wild", Proceedings of the 2019 CHI Conference on Human Factors in Computing Systems, May 2019, pp. 1-12.

Extended European Search Report received for corresponding European Patent Application No. 19197433.6, dated Mar. 10, 2020, 8 pages.

* cited by examiner

EYEWEAR DEVICE

FIELD

The present specification relates to eye and eyelid movement.

BACKGROUND

One or more devices may be used for monitoring eye and eyelid movement. There remains a need for further improvements in this field.

SUMMARY

In a first aspect, this specification describes an apparatus (such as eyeglasses or some other eyewear device) comprising: a first device electrode provided on a first portion of an eyewear device, wherein the first device electrode is configured to form a first capacitor with a first eyelid electrode provided on a first eyelid of a user, wherein the first capacitor has a first capacitance; a second device electrode provided on a second portion of the eyewear device, wherein the second device electrode is configured to form a second capacitor with a second eyelid electrode provided on a second eyelid of the user, wherein the second capacitor has a second capacitance; means for applying an electrical signal to a first electrical circuit, wherein the first electrical circuit is formed between: the first device electrode and the first eyelid electrode, an eyeball electrical path between the first eyelid electrode and the second eyelid electrode, the second eyelid electrode and the second device electrode, and the second device electrode and the first device electrode; and means for determining current and/or voltage measurements of the first electrical circuit, wherein the current and/or voltage measurements are usable for determining heart rate data and eyelid movement data for the user. Some embodiments further comprise means for determining heart rate data and eyelid movement data for the user based on one or more changes in said current and/or voltage measurements of the first electrical circuit.

The means for determining heart rate data and eyelid movement data may be configured to determine eyelid movement data by determining a first increase (e.g. an increase having a level above a first threshold (larger than the second threshold referred to below) and/or a duration longer than a first duration (longer than the second duration referred to below) in the current and/or voltage measurements, wherein the first increase is caused by an increase in at least one of the first capacitance and second capacitance. A duration of the first increase may be used for determining a duration of a first eyelid movement. The increase in at least one of the first capacitance and the second capacitance may be based on a decrease in at least one of a first distance between the first device electrode and the first eyelid electrode, and a second distance between the second device electrode and the second eyelid electrode, wherein the decrease is caused by the first eyelid movement.

The means for determining heart rate data and eyelid movement data may be configured to determine heart rate by determining a second increase (e.g. an increase having a level above a second threshold (smaller than the first threshold referred to above) and/or a duration longer than a second duration (shorter than the first duration referred to above) in the first current and/or voltage measurement; wherein the second increase is used for determining an increase in a first impedance of the eyeball electrical path due to changes in blood concentration during a plurality of heartbeats, wherein a frequency of the increase in the first impedance is used for determining the heart rate data, and wherein the first impedance is formed from an effective eyeball resistance and eyeball capacitance of the eyeball of the user.

In some embodiments, eyelid movement data and heart rate data are distinguished based on differences in at least one of frequency, duration or amplitude of the first increase and the second increase. The first increase may have higher amplitude relative to the second increase. The first increase may have a lower frequency relative to the second increase.

The determined eyelid movement data and heart rate data may be used for determining communication from the user and physiological data of the user respectively.

In a second aspect, this specification describes an apparatus (such as a control module) comprising: means for applying an electrical signal to a first electrical circuit, wherein the first electrical circuit is formed between: a first device electrode and a first eyelid electrode, an eyeball electrical path between the first eyelid electrode and a second eyelid electrode, the second eyelid electrode and a second device electrode, and the second device electrode and the first device electrode; wherein, the first device electrode is configured to be provided on a first portion of an eyewear device, the second device electrode is configured to be provided on a second portion of the eyewear device, the first eyelid electrode is configured to be provided on a first eyelid of a user, and the second eyelid electrode is configured to be provided on a second eyelid of the user; wherein, the first device electrode is configured to form a first capacitor with the first eyelid electrode, wherein the first capacitor has a first capacitance; and the second device electrode is configured to form a second capacitor with the second eyelid electrode, wherein the second capacitor has a second capacitance; means for determining current and/or voltage measurements of the first electrical circuit, wherein a current and/or voltage is generated in the first electrical circuit in response to the applied electrical signal; and means for determining heart rate data and eyelid movement data for the user based on one or more changes in the current and/or a voltage measurements.

The means for determining heart rate data and eyelid movement data may be configured to determine eyelid movement data by determining a first increase (e.g. an increase having a level above a first threshold (larger than the second threshold referred to below) and/or a duration longer than a first duration (longer than the second duration referred to below) in the current and/or voltage measurements, wherein the first increase is caused by an increase in at least one of the first capacitance and second capacitance. A duration of the first increase may be used for determining a duration of a first eyelid movement. The increase in at least one of the first capacitance and the second capacitance may be based on a decrease in at least one of a first distance between the first device electrode and the first eyelid electrode, and a second distance between the second device electrode and the second eyelid electrode, wherein the decrease is caused by the first eyelid movement.

In some embodiments, the means for determining heart rate data and eyelid movement data is configured to determine heart rate by determining a second increase (e.g. an increase having a level above a second threshold (smaller than the first threshold referred to above) and/or a duration longer than a second duration (shorter than the first duration referred to above) in the first current and/or voltage measurement; wherein the second increase is used for determining an increase in a first impedance of the eyeball electrical path due to changes in blood concentration during a plurality of heartbeats, wherein a frequency of the increase in the first impedance is used for determining the heart rate data, and wherein the first impedance is formed from an effective eyeball resistance and eyeball capacitance of the eyeball of the user.

In some embodiments, the eyelid movement data and heart rate data are distinguished based on differences in at least one of frequency, duration or amplitude of the first increase and the second increase. The first increase may have a higher amplitude relative to the second increase. The first increase may have a lower frequency relative to the second increase.

The determined eyelid movement data and heart rate data may be used for determining communication from the user and physiological data of the user respectively.

In a third aspect, this specification describes an apparatus as described with reference to any one of the first to third aspects, wherein the means comprise: at least one processor; and at least one memory including computer program code, the at least one memory and the computer program configured, with the at least one processor, to cause the apparatus to perform: applying the electrical signal to the first electrical circuit; and determining the current and/or voltage measurements of the first electrical circuit, wherein the current and/or voltage measurements are usable for determining heart rate data and eyelid movement data for the user.

In a fourth aspect, this specification describes an apparatus (e.g. eyelid electrodes) comprising: a first eyelid electrode configured to be provided on a first eyelid of a user, wherein the first eyelid electrode is configured to form a first capacitor with a first device electrode provided on a first portion of an eyewear device, wherein the first capacitor has a first capacitance; a second eyelid electrode configured to be provided on the second eyelid of the user, wherein the second eyelid electrode is configured to form a second capacitor with a second device electrode provided on a second portion of the eyewear device, wherein the second capacitor has a second capacitance; and wherein, in use, an eyeball electrical path is formed between the first eyelid electrode and the second eyelid electrode, such that a first electrical circuit is formed between the first device electrode and the first eyelid electrode, the eyeball electrical path, the second eyelid electrode and the second device electrode, and the second device electrode and the first device electrode.

In a fifth aspect, this specification describes a method comprising: applying an electrical signal to a first electrical circuit, wherein the first electrical is circuit is formed between: a first device electrode and a first eyelid electrode, wherein: the first device electrode is configured to be provided on a first portion of an eyewear device; the first eyelid electrode is configured to be provided on a first eyelid of a user; the first device electrode forms a first capacitor with the first eyelid electrode; and the first capacitor has a first capacitance; an eyeball electrical path between the first eyelid electrode and a second eyelid electrode; the second eyelid electrode and a second device electrode, wherein: the second device electrode is configured to be provided on a second portion of the eyewear device; the second eyelid electrode is configured to be provided on a second eyelid of the user; the second device electrode forms a second capacitor with the second eyelid electrode; and the second capacitor has a second capacitance; and the second device electrode and the first device electrode; and determining current and/or voltage measurements of the first electrical circuit, wherein the current and/or voltage measurements are usable for determining heart rate data and eyelid movement data for the user.

The method may further comprise determining heart rate data and eyelid movement data for the user based on one or more changes in said current and/or voltage measurements of the first electrical circuit.

Determining heart rate data and eyelid movement data may comprise determining eyelid movement data by determining a first increase (e.g. an increase having a level above a first threshold (larger than the second threshold referred to below) and/or a duration longer than a first duration (longer than the second duration referred to below) in the current and/or voltage measurements, wherein the first increase is caused by an increase in at least one of the first capacitance and second capacitance. A duration of the first increase may be used for determining a duration of a first eyelid movement. The increase in at least one of the first capacitance and the second capacitance may be based on a decrease in at least one of a first distance between the first device electrode and the first eyelid electrode, and a second distance between the second device electrode and the second eyelid electrode, wherein the decrease is caused by the first eyelid movement.

Determining heart rate data and eyelid movement data may comprising determining heart rate by determining a second increase (e.g. an increase having a level above a second threshold (smaller than the first threshold referred to above) and/or a duration longer than a second duration (shorter than the first duration referred to above) in the first current and/or voltage measurement; wherein the second increase is used for determining an increase in a first impedance of the eyeball electrical path due to changes in blood concentration during a plurality of heartbeats, wherein a frequency of the increase in the first impedance is used for determining the heart rate data, and wherein the first impedance is formed from an effective eyeball resistance and eyeball capacitance of the eyeball of the user.

In some embodiments, the eyelid movement data and heart rate data are distinguished based on differences in at least one of frequency, duration or amplitude of the first increase and the second increase. For example, the first increase may have higher amplitude relative to the second increase and/or the first increase may have a lower frequency relative to the second increase.

The determined eyelid movement data and heart rate data may be used for determining communication from the user and physiological data of the user respectively.

In a sixth aspect, this specification describes an apparatus configured to perform any method as described with reference to the fifth aspect.

In a seventh aspect, this specification describes computer-readable instructions which, when executed by computing apparatus, cause the computing apparatus to perform any method as described with reference to the fifth aspect.

In an eighth aspect, this specification describes a computer readable medium comprising program instructions stored thereon for performing at least the following: applying an electrical signal to a first electrical circuit formed between a first device electrode and a first eyelid electrode, an eyeball electrical path between the first eyelid electrode and a second eyelid electrode, the second eyelid electrode and a second device electrode, and the second device electrode and the first device electrode; wherein the first device electrode is configured to be provided on a first portion of an eyewear device, the second device electrode is configured to be provided on a second portion of the eyewear device, the first eyelid electrode is configured to be provided on a first eyelid of a user, and the second eyelid electrode is configured to be provided on a second eyelid of the user; wherein, the first device electrode is configured to form a first capacitor with the first eyelid electrode, wherein the first capacitor has a first capacitance; and wherein the second device electrode is configured to form a second capacitor with the second eyelid electrode provided on the second eyelid of the user, wherein the second capacitor has a second capacitance; and determining current and/or voltage measurements of the first electrical circuit, wherein a current and/or voltage is generated in the first electrical circuit in response to the applied electrical signal. The program instructions may be further perform: determining heart rate data and eyelid movement data for the user based on one or more changes in the current and/or voltage measurements.

In a ninth aspect, this specification describes a computer program comprising instructions for causing an apparatus to perform at least the following: applying an electrical signal to a first electrical circuit formed between a first device electrode and a first eyelid electrode, an eyeball electrical path between the first eyelid electrode and a second eyelid electrode, the second eyelid electrode and a second device electrode, and the second device electrode and the first device electrode; wherein the first device electrode is configured to be provided on a first portion of an eyewear device, the second device electrode is configured to be provided on a second portion of the eyewear device, the first eyelid electrode is configured to be provided on a first eyelid of a user, and the second eyelid electrode is configured to be provided on a second eyelid of the user; wherein, the first device electrode is configured to form a first capacitor with the first eyelid electrode, wherein the first capacitor has a first capacitance; and wherein the second device electrode is configured to form a second capacitor with the second eyelid electrode provided on the second eyelid of the user, wherein the second capacitor has a second capacitance; and determining current and/or voltage measurements of the first electrical circuit, wherein a current and/or voltage is generated in the first electrical circuit in response to the applied electrical signal. The computer program may further cause the apparatus to perform: determining heart rate data and eyelid movement data for the user based on one or more changes in the current and/or voltage measurements.

In a tenth aspect, this specification describes an apparatus comprising: at least one processor; and at least one memory including computer program code which, when executed by the at least one processor, causes the apparatus to: apply an electrical signal to a first electrical circuit formed between a first device electrode and a first eyelid electrode, an eyeball electrical path between the first eyelid electrode and a second eyelid electrode, the second eyelid electrode and a second device electrode, and the second device electrode and the first device electrode; wherein the first device electrode is configured to be provided on a first portion of an eyewear device, the second device electrode is configured to be provided on a second portion of the eyewear device, the first eyelid electrode is configured to be provided on a first eyelid of a user, and the second eyelid electrode is configured to be provided on a second eyelid of the user; wherein, the first device electrode is configured to form a first capacitor with the first eyelid electrode, wherein the first capacitor has a first capacitance; and wherein the second device electrode is configured to form a second capacitor with the second eyelid electrode provided on the second eyelid of the user, wherein the second capacitor has a second capacitance; and determine current and/or voltage measurements of the first electrical circuit, wherein a current and/or voltage is generated in the first electrical circuit in response to the applied electrical signal. The code, when executed, may further cause the apparatus to: determine heart rate data and eyelid movement data for the user based on one or more changes in the current and/or voltage measurements.

In an eleventh aspect, this specification describes an apparatus (such as eyeglasses or some other eyewear device) comprising: a first device electrode provided on a first portion of an eyewear device, wherein the first device electrode is configured to form a first capacitor with a first eyelid electrode provided on a first eyelid of a user, wherein the first capacitor has a first capacitance; a second device electrode provided on a second portion of the eyewear device, wherein the second device electrode is configured to form a second capacitor with a second eyelid electrode provided on a second eyelid of the user, wherein the second capacitor has a second capacitance; a voltage source (e.g. an AC voltage source) for applying an electrical signal to a first electrical circuit, wherein the first electrical circuit is formed between: the first device electrode and the first eyelid electrode, an eyeball electrical path between the first eyelid electrode and the second eyelid electrode, the second eyelid electrode and the second device electrode, and the second device electrode and the first device electrode; and a processor for determining current and/or voltage measurements of the first electrical circuit, wherein the current and/or voltage measurements are usable for determining heart rate data and eyelid movement data for the user.

In a twelfth aspect, this specification describes an apparatus (such as a control module) comprising: a voltage source (e.g. an AC voltage source) for applying an electrical signal to a first electrical circuit, wherein the first electrical circuit is formed between: a first device electrode and a first eyelid electrode, an eyeball electrical path between the first eyelid electrode and a second eyelid electrode, the second eyelid electrode and a second device electrode, and the second device electrode and the first device electrode; wherein, the first device electrode is configured to be provided on a first portion of an eyewear device, the second device electrode is configured to be provided on a second portion of the eyewear device, the first eyelid electrode is configured to be provided on a first eyelid of a user, and the second eyelid electrode is configured to be provided on a second eyelid of the user; wherein, the first device electrode is configured to form a first capacitor with the first eyelid electrode, wherein the first capacitor has a first capacitance; and the second device electrode is configured to form a second capacitor with the second eyelid electrode, wherein the second capacitor has a second capacitance; a measurement device (e.g. a voltmeter, ammeter or the like) for determining current and/or voltage measurements of the first electrical circuit, wherein a current and/or voltage is generated in the first electrical circuit in response to the applied electrical signal; and a processor for determining heart rate data and eyelid movement data for the user based on one or more changes in the current and/or a voltage measurements.

BRIEF DESCRIPTION OF THE DRAWINGS

Example embodiments will now be described, by way of example only, with reference to the following schematic drawings, in which.

DETAILED DESCRIPTION

Figure 1:
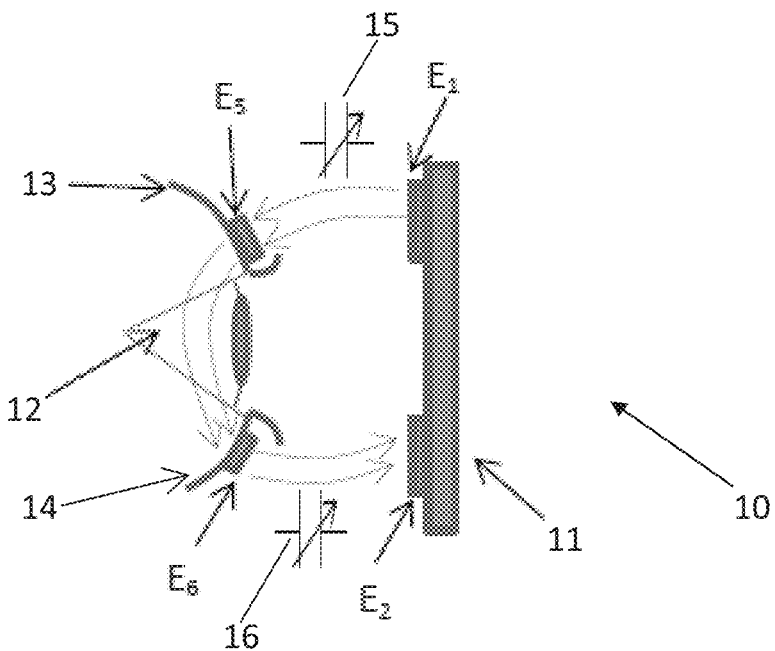
FIG. 1 is a block diagram of a system in accordance with an example embodiment.

The scope of protection sought for various embodiments of the invention is set out by the independent claims. The embodiments and features, if any, described in the specification that do not fall under the scope of the independent claims are to be interpreted as examples useful for understanding various embodiments of the invention.

In the description and drawings, like reference numerals refer to like elements throughout.

FIG. 1 is a block diagram of a system, indicated generally by the reference numeral 10, in accordance with an example embodiment. System 10 comprises a first device electrode E1 provided on a first portion of an eyewear device 11 and a second device electrode E2 provided on a second portion of the eyewear device 11. The system 10 further comprises a first eyelid electrode E5 provided on a first eyelid 13 (e.g. upper eyelid) of a user, and a second eyelid electrode E6 provided on a second eyelid 14 (e.g. lower eyelid) of the user. The first device electrode E1 may form a first capacitor 15 with the first eyelid electrode E5, such that the first capacitor 15 may have a first capacitance. The arrows shown in the direction of the first eyelid electrode E5 from the first device electrode E1 may represent a direction of the electrical flux between the first eyelid electrode E5 and the first device electrode E1. The second device electrode E2 may form a second capacitor 16 with the second eyelid electrode E6, such that the second capacitor 16 may have a second capacitance. The arrows shown in the direction of the second device electrode E2 from the second eyelid electrode E6 may represent a direction of the electrical flux between the second device electrode E2 and the second eyelid electrode E6. An eyeball electrical path 12 may be formed through the user's eyeball between the first eyelid electrode E5 and the second eyelid electrode E6. The arrows shown in the direction of the second eyelid electrode E6 from the first eyelid electrode E5 may represent a direction of the electrical flux between the second eyelid electrode E6 and the first eyelid electrode E5. In an example embodiment, a first electrical circuit may be formed between the first device electrode E1 and the first eyelid electrode E5, the eyeball electrical path 12 between the first eyelid electrode E5 and the second eyelid electrode E6, and the second device electrode E2. The first electrical circuit may be formed when an electrical signal is applied, for example, at the eyewear device 11. In an example embodiment, current and/or voltage measurements of the first electrical circuit may be usable for determining heart rate data and eyelid movement data of the user.

Figure 2:
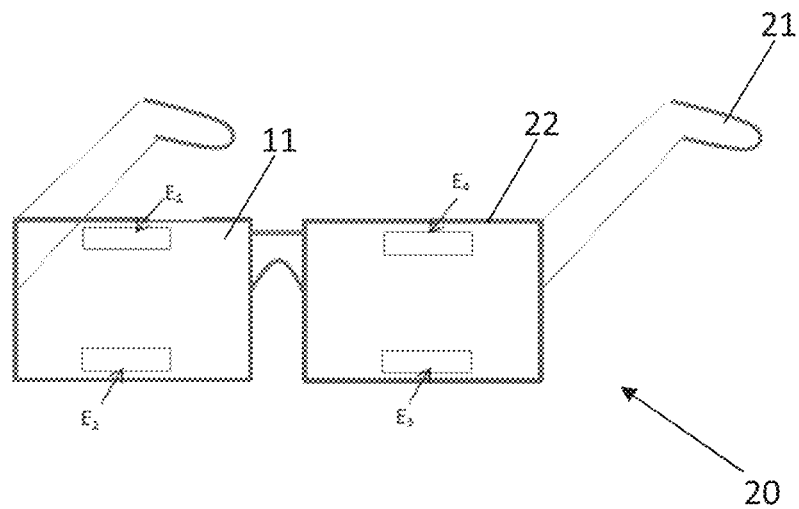
FIG. 2 shows a system in accordance with an example embodiment.

FIG. 2 shows a system, indicated generally by the reference numeral 20, in accordance with an example embodiment. System 20 comprises eyeglasses 21, such that the eyewear device 11 (described above with reference to FIG. 1) forms a part of the eyeglasses 21. Eyeglasses 21 may comprise one or more eyewear devices including the eyewear device 11 and an eyewear device 22. For example, the eyewear device 11 may comprise electrodes (e.g. the first device electrode E1 and the second device electrode E2) for forming the first electrical circuit with one eye (on which the first and second eyelid electrodes E5 and E6 are provided) of the user, and the eyewear device 22 may comprise device electrodes E4 and E3 for forming a second electrical circuit with the other eye of the user, where the other eye may also comprise eyelid electrodes similar to the first and second eyelid electrodes E5 and E6. In an example embodiment, one or more of the device electrodes E1, E2, E3, and E4 may be provided on one or more portions of lenses or frames of the eyeglasses 21. In one example embodiment, current and/or voltage measurements from one or both of the first and second electrical circuits may be used for determining eyelid movement data and heart rate data. For example, the first electrical circuit may be used for determining the eyelid movement data and heart rate data, and the second electrical circuit may be used as an additional circuit for confirming the eyelid movement data and heart rate data determined from the first electrical circuit. Alternatively, only one of the first electrical circuit and second electrical circuit may be used for determining the eyelid movement data and heart rate data. Alternatively, or in addition, current and/or voltage measurements from the first electrical circuit and the second electrical circuit may be combined (e.g. averaged, etc.) in order to determine the eyelid movement data and heart rate data.

It may be appreciated that the example embodiments may be implemented with one eyewear device (such as the eyewear device 11), such that the eyewear device 22 may not be required. In some example embodiments, the eyewear device (such as the eyewear device 11) may be comprised within eyewear frames without lenses, other forms of headwear, a virtual reality headset, a device used by medical professionals (e.g. optician) for applying to a user's eye, a telescope, periscope, binoculars, or any other device or eyewear that may be worn by a user or may be provided near the eye of the user.

It may be appreciated that eyelid movement detection may be used for assistive technologies for people with one or more disorders (such as Amyotrophic lateral sclerosis (ALS) disease). ALS patients may use eyelid movement for communication, as they may have limited or no functionality of voluntary controlled muscles. Assisted communication for ALS patients may be employed using a brain-computer interface that utilizes signals from the brain for allowing the patients to communicate, which may require high processing demands for brain-computer machines and may have contact issues on brain-computer interfaces. Electrooculography (EOG) may also be used for eyelid movement detection. EOG may require conductive gel application due to electrode-skin contact, which may sometimes cause skin irritation, or the contact quality may sometimes be affected by gel dehydration.

Some example embodiments describe apparatus and methods for determining eyelid movement data and heart rate data at the same device (e.g. the eyewear device 11). As such, a single device may be used both for determining eyelid movement data (e.g. using capacitive based eyelid movement detection) and heart rate data (e.g. using impedance plethysmography). For example, eyelid movement detection may enable communication with ALS patients, while the heart rate detection may provide insight on stress level and/or other body conditions which may be estimated using the heart rate data.

Figure 3:
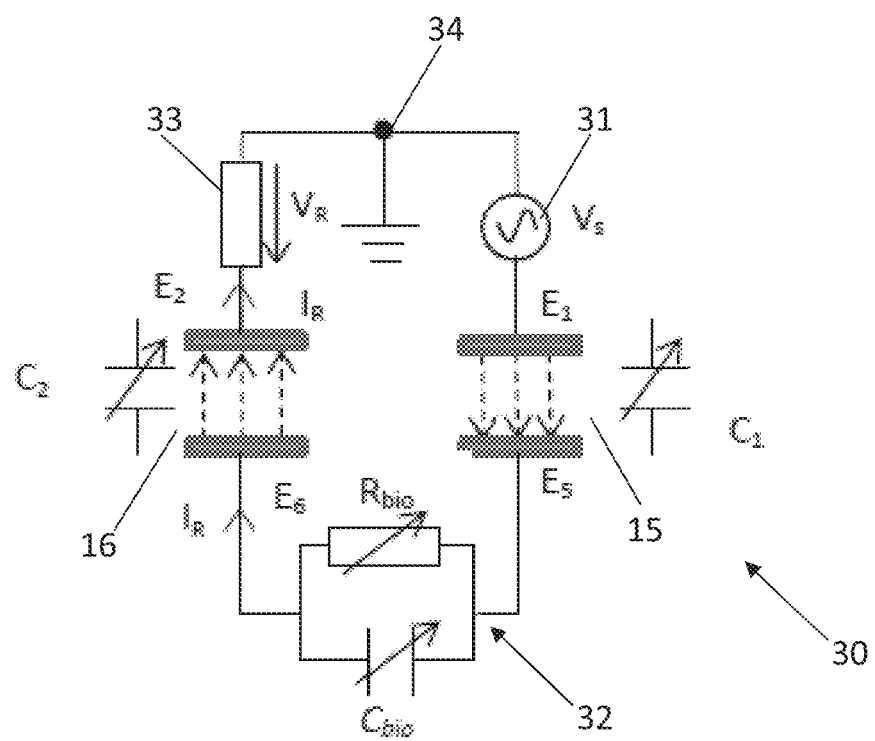
FIG. 3 is a block diagram of a system in accordance with an example embodiment.

FIG. 3 is a block diagram of a system comprising a first electrical circuit, indicated generally by the reference numeral 30, in accordance with an example embodiment. The first electrical circuit 30 may be similar to the first electrical circuit described above with reference to FIG. 1. The first electrical circuit 30 comprises a voltage source 31 (for example, an alternating voltage (AV) source connected to a power supply), a first capacitor 15 having a first capacitance (e.g. variable capacitance C1) formed between the first device electrode E1 and the first eyelid electrode E5, a second capacitor 16 having a second capacitance (e.g. variable capacitance C2) formed between the second device electrode E2 and the second eyelid electrode E6, an eyeball electrical path 32 between the first eyelid electrode E5 and the second eyelid electrode E6 (where the eyeball electrical path 32 may have a first impedance due to an effective eyeball resistance $R_{bio}$ and an effective eyeball capacitance $C_{bio}$), an effective circuit resistance 33, and a ground connection 34. Current and/or voltage through the first electrical circuit may be an effective current $I_R$ and an effective voltage $V_R$ respectively, such that the effective current $I_R$ and/or the effective voltage $V_R$ may be dependent upon changes in capacitance through the circuit and/or changes in impedance.

Figure 4:
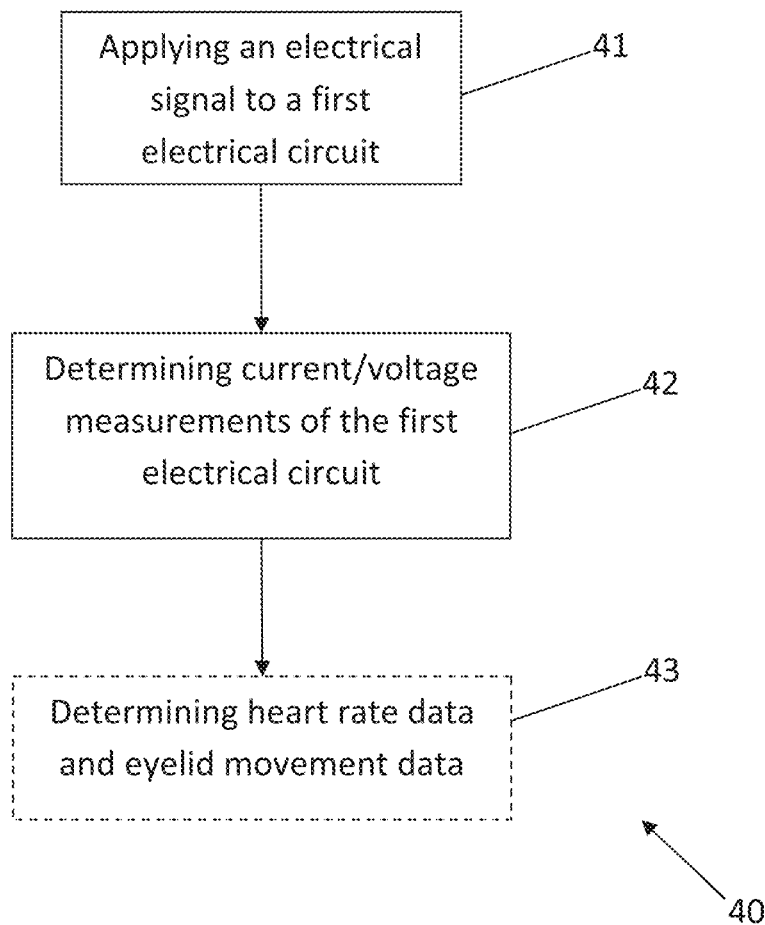
FIG. 4 is a flowchart showing an algorithm in accordance with example embodiments.

FIG. 4 is a flowchart of an algorithm, indicated generally by the reference numeral 40, in accordance with an example embodiment. FIG. 4 may be viewed in conjunction with FIG. 3 for better understanding of the example embodiments.

At operation 41, an electrical signal may be applied to the first electrical circuit 30. For example, an electrical signal may be applied at or by the voltage source 31. In an example embodiment, the voltage source 31 and the ground connection 34 may be provided at the eyewear device 11. The voltage applied at the voltage source 31 may be an alternating voltage to facilitate capacitive coupling between the eyelid electrodes and the device electrodes. In an example, the magnitude of the voltage applied at the voltage source 31 may remain constant throughout the operation of the first electrical circuit 30, such that any changes in the magnitude of the effective current and voltage measurements are not caused due to changes in the magnitude of the voltage applied. In an example, the voltage source 31 (e.g. an alternating voltage source) and ground connection 34 may be connected to a circuit power supply (e.g. a battery, a rechargeable battery, solar powered battery, or the like) with at least one converter for providing alternating voltage at the voltage source 31.

At operation 42, at least one of the current measurements (e.g. magnitude of $I_R$) and the voltage measurements (e.g. magnitude of $V_R$) of the first electrical circuit 30 is measured (for example, using an ammeter, a voltmeter, or the like). The current and voltage measurements may relate to the effective current and voltage through the first electrical circuit 30. Determining the current and/or voltage measurements may comprise detecting any changes in the current and/or voltage measurements. The changes in the current and voltage measurements may be recorded (e.g. in the form of a waveform), such that the recorded changes may comprise information regarding at least one of duration of changes, frequency of changes, amplitude of changes, or the like. The determined current and voltage measurements may be usable for determining heart rate data and eyelid movement data for the user.

At operation 43 (which operation may be optional), heart rate data and eyelid movement data of the user may be determined, at least partially based on the determined current and/or voltage measurements of the first electrical circuit.

In an example embodiment, changes in the effective first capacitance C1 and second capacitance C2 may cause changes in the effective current and voltage measurements of the first electrical circuit 30. Similarly, changes in the first impedance of the eyeball electrical path may also cause changes in the effective current and voltage measurements of the first electrical circuit 30. When eyelids of the user are moved (e.g. when the eyelids are closed or opened), there may be changes in a first distance (e.g. horizontal distance, vertical distance, or diagonal distance) between the first device electrode E1 and the first eyelid electrode E5, and a second distance (e.g. horizontal distance, vertical distance, or diagonal distance) between the second device electrode E2 and the second eyelid electrode E6. For example, with reference to FIG. 1, when the user closes the eyelids 13 and 14, the first distance and/or the second distance may decrease. The decrease in the first distance may cause the first capacitance C1 to increase (as the capacitance increases when the electrodes are closer to each other) and the decrease in the second distance may cause the second capacitance C2 to increase. The increase in at least one of the first capacitance C1 and the second capacitance C2 may cause a first increase in the current and/or voltage measurements of the first electrical circuit 30. Subsequently, when the eyelid is opened again, the first distance and the second distance may increase, and thus the first capacitance C1 and the second capacitance C2 may decrease, causing the current and/or voltage measurements to decrease.

In an example embodiment, changes in the first impedance of the eyeball electrical path 32 may cause changes in the effective current and voltage measurements of the first electrical circuit 30. During a heartbeat of the user, the blood concentration (e.g. volume of blood) in the eyeball of the user may be increased. The increase in blood concentration may cause changes in $R_{bio}$ and $C_{bio}$, such that the first impedance is increased. The increase in the first impedance may cause a second increase in the current and/or voltage measurements. Subsequently, after the heartbeat, the first impedance may decrease, and thus may cause the current and/or voltage measurements to decrease.

Figure 5:
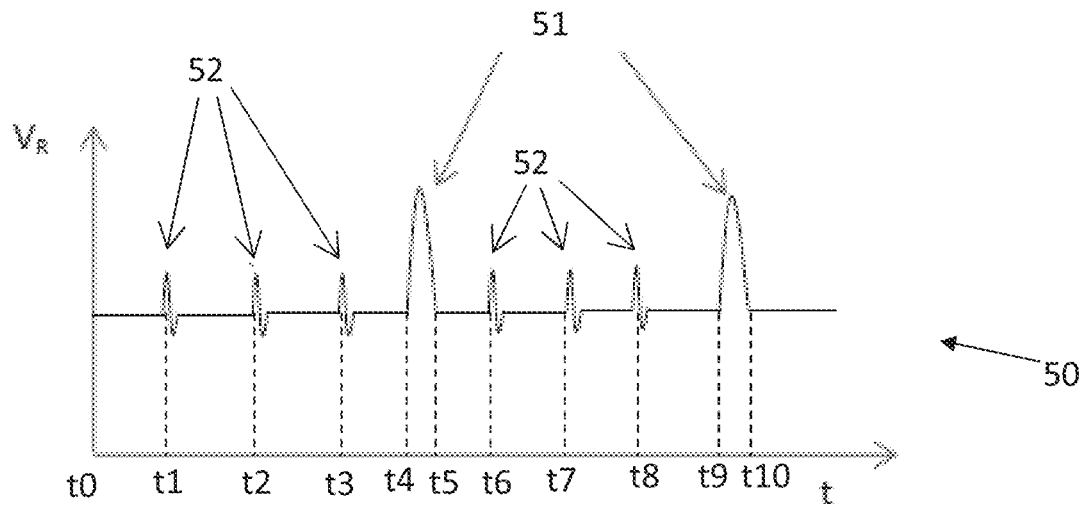
FIGS. 5 and 6 are plots of data obtained in accordance with an example embodiment.

FIG. 5 is a plot, indicated by the reference numeral 50, of data obtained in accordance with some example embodiments. Plot 50 shows changes in magnitude (e.g. amplitude) of an effective voltage measurement ($V_R$) with respect to time (t). The data for plot 50 may be obtained by monitoring current and/or voltage measurements of the first electrical circuit 30. It may be appreciated that a plot showing changes in an effective current measurement ($I_R$) with respect to time may have similar rises and falls as the plot 50. Plot 50 comprises a plurality of first increases 51 and a plurality of second increases 52. One or more of the first increases 51 and second increases 52 may form part of pulses, such that the current and/or voltage measurements may fall and/or rise after the first increases 51 and/or after the second increases 52. The first increases 51 are caused due to eyelid movement (e.g. closing eyelids), and the second increases 52 are caused due to heartbeats. As such, the eyelid movement data may be determined based at least partially on the first increases 51 in the current and/or voltage measurements, and the heart rate data may be determined based at least partially on the second increases 52 in the current and/or voltage measurements. In an example embodiment, as shown in the plot 50, the first increases 51 in current and/or voltage measurements caused due to eyelid movement may have higher amplitude relative to the second increase in current and/or voltage measurements caused due to heartbeats. For example, when the eyelids are open (e.g. time t0 to time t4 and from t5 to time t9), the first capacitance C1 and the second capacitance C2 may have a value dependent on the voltage applied at the voltage source 31 (as well as being dependent on factors such as the size of the eyelid electrodes and device electrodes, type of dielectric (e.g. air) between the eyelid electrodes and device electrodes, and/or distance between the eyelid electrodes and device electrodes etc.). When the eyelids are open, the first capacitance C1 and second capacitance C2 may remain constant (or substantially constant), as the distance between the eyelid electrodes and the device electrodes may not change substantially. During the time period (e.g. time t0 to time t4) when the eyelids are open, the heartbeats of the user may cause the second increases 52. The frequency of heartbeats may be higher than the frequency of eyelid blinking, as normally a user would blink less often than the user's heart would beat. For example, from the plot 50, it may be determined that a heartbeat occurs at least at the times t1, t2, t3, t6, t7, and t8. For example, the heart rate may be calculated based on the information in the plot 50, for example, indicating that the heart beats thrice in a time period of t0 to t3. As the first impedance of the eyeball electrical path is relatively small compared to the impedance of the first electrical circuit 30, the first increases 51 caused by the changes in the capacitances C1 and C2 have higher amplitudes compared to the second increases 52 caused by the changes in the first impedance. As such, the first increase 51 at time period t4 to t5 and at time period t9 to t10 is at least partially (mostly) due to the changes in capacitances C1 and C2 (e.g. eyelid movement). There may be one or more heartbeats in the time period of t4 to t5 or in the time period of t9 to t10. However, the high amplitude of the first increases 51 are caused by the eyelid movement. The plot 50 may be used for determining duration (e.g. t4 to t5; t9 to t10) or frequency of eyelid movement (e.g. eyelid blinking occurs once in the time period of t0 to t5, and the eyes are closed for the duration of t4 to t5).

Figure 6:
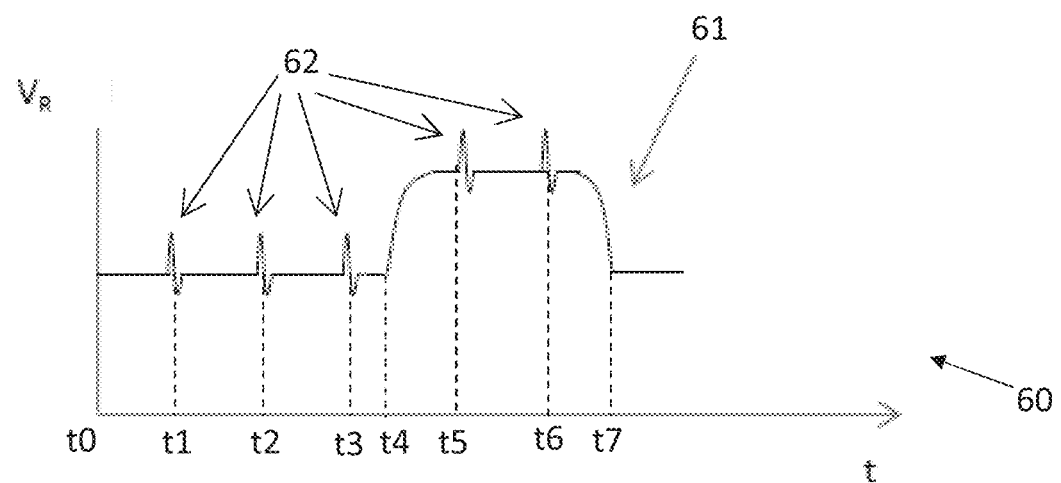

FIG. 6 is a plot, indicated by the reference numeral 60, of data obtained in accordance with some example embodiments. Plot 60 shows changes in magnitude (e.g. amplitude) of an effective voltage measurement ($V_R$) with respect to time (t). It may be appreciated that a plot showing changes in an effective current measurement ($I_R$) with respect to time may have similar rises and falls as the plot 60. Plot 60 comprises a first increase 61 and a plurality of second increases 62. The first increase 61 is caused due to eyelid movement (e.g. closing eyelids), and the second increases 62 are caused due to heartbeats. As such, the eyelid movement data may be determined based at least partially on the first increase 61 in the current and/or voltage measurements, and the heart rate data may be determined based at least partially on the second increases 62 in the current and/or voltage measurements. The first increase 61 of plot 60 shows that the eyelids of the user were closed for a longer period of time (e.g. t4 to t7) compared to the first increases 51 of plot 50. The plot 60 shows two of the plurality of second increases 62 occurring at t5 and t6, which is within the duration (t4 to t7) in which the eyelids were closed. As such, the second increases 62 indicate that there were at least two heartbeats of the user within the duration of t4 to t7 when the user kept the eyelids closed.

Figure 7:
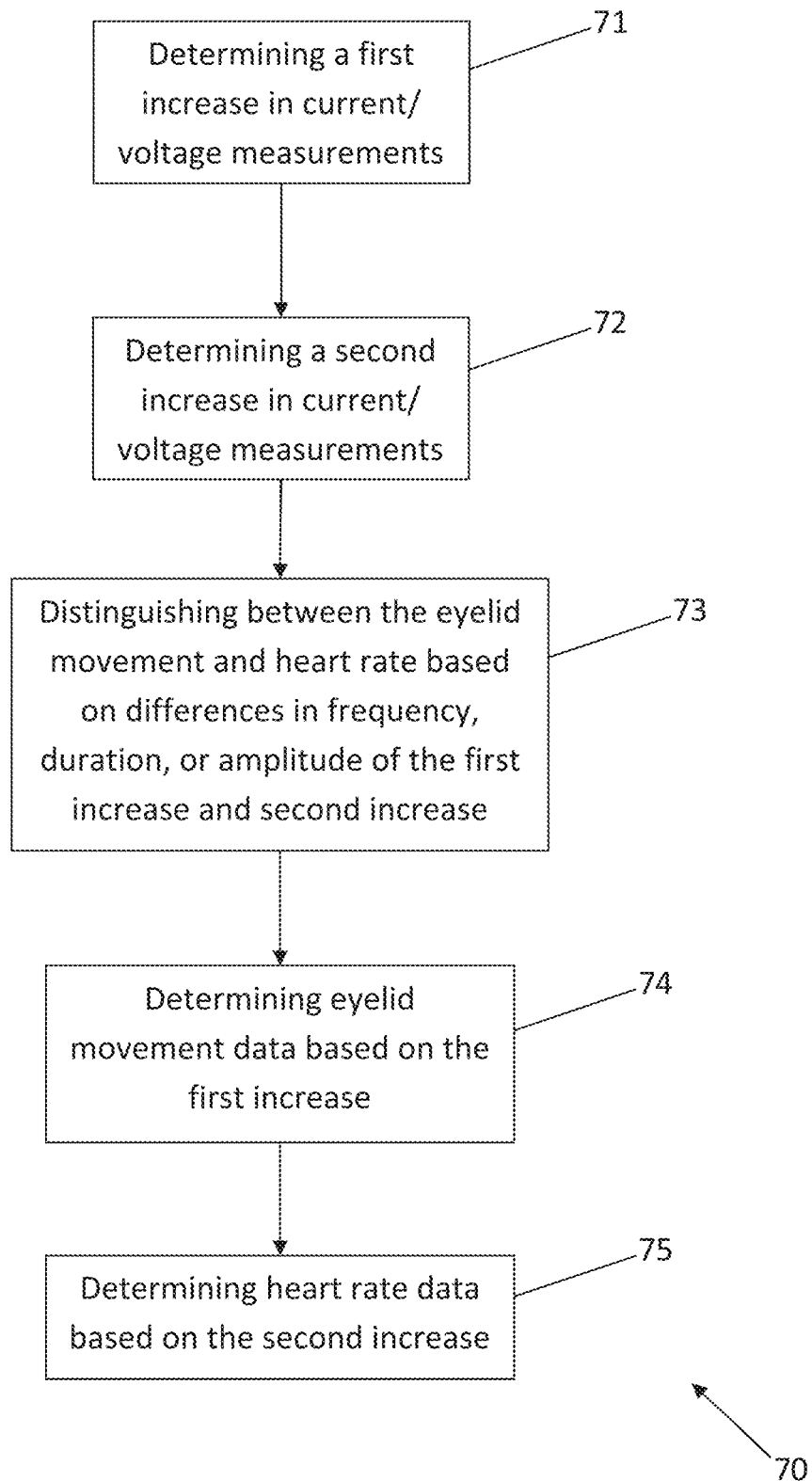
FIG. 7 is a flowchart showing an algorithm in accordance with an example embodiment.

FIG. 7 is a flowchart of an algorithm, indicated generally by the reference numeral 70, in accordance with an example embodiment. The operations of algorithm 70 may be used for determining eyelid movement data and/or heart rate data based on current and/or voltage measurements of the first electrical circuit 30. FIG. 7 may be viewed in conjunction with the plots of FIGS. 5 and 6.

At operation 71, at least one first increase (e.g. 51 or 61) in the current and/or voltage measurements is determined. As described above, the first increase may be caused by an increase in at least one of the first capacitance C1 and the second capacitance C2.

At operation 72, at least one second increase (e.g. 52 or 62) in the current and/or voltage measurements is determined. As described above, the second increase may be caused by heartbeats.

At operation 73, the eyelid movement data and the heart rate data are distinguished based on differences in at least one of frequency, duration or amplitude of the first increase and the second increase. As described above, amplitude of increase in current and/or voltage measurements is expected to be higher for eyelid movements compared to that for heartbeats. Similarly, frequency of increases in current and/or voltage measurements is expected to be lower for eyelid movements compared to that for heartbeats. As such, with reference to FIG. 5, the differences in amplitude and frequency of the first increases 51 and the second increases 52 may indicate that the reason for the first increases 51 is different than that for the second increases 52. As such, the first increases 51 may be distinguished from the second increases 52 based on the amplitude, frequency, and/or duration of the increases. For example, the amplitude of the first increases (51, 61) may be higher than a first threshold increase and the amplitude of the second increases (52, 62) may be higher than a second threshold increase. The first threshold increase may be defined as being related to eyelid movement, the second threshold increase may be defined as being related to heartbeats, and the first threshold increase may be higher than the second threshold increase. The duration of the first increases (51, 61) may be higher than a first threshold duration and the duration of the second increases (52, 62) may be higher than a second threshold duration. The first threshold duration may be defined as being related to eyelid movement, the second threshold duration may be defined as being related to heartbeats, and the first threshold duration may be higher than the second threshold duration. The frequency of the first increases (51, 61) may be lower than a first threshold frequency and the frequency of the second increases (52, 62) may be lower than a second threshold frequency. The first threshold frequency may be defined as being related to eyelid movement, the second threshold frequency may be defined as being related to heartbeats, and the first threshold frequency may be lower than the second threshold frequency (as eye blinking may occur less frequently compared to heartbeats).

At operation 74, eyelid movement data may be determined based on the first increase (51 or 61). As the first increases and the second increases are distinguished at operation 73, the second increases may be disregarded for determination of the eyelid movement data. For example, with reference to the plot 50, it may be determined that the user closes the eyelids at times t4 and t9, and the duration for which the eyelids remain closed may be the time period t4 to t5 and t9 to t10 respectively. With reference to plot 60, it may be determined that the user closes the eyelids at time t4 and opens the eyelid at time t7, such that the duration for which the eyelids remain closed may be the time period t4 to t7.

At operation 75, heart rate data may be determined based on two or more of the plurality of the second increases (52 or 62). As the first increases and the second increases are distinguished at operation 73, the first increases may be disregarded for determination of the heart rate data. For example, with reference to the plot 50, there are at least three heartbeats within the period of t0 to t4 at times t1, t2, t3, and at least three heartbeats within the period of t5 to t9 at times t6, t7 and t8. The information from plot 50 may therefore be used for determining the heart rate data of the user.

Some of the operations of the algorithm 70 may be omitted in some example embodiments. For example, a variant of the algorithm 70 may be used where only eyelid movement data is of interest. A further variant of the algorithm 70 may be used where only heart rate data is of interest.

Figure 8:
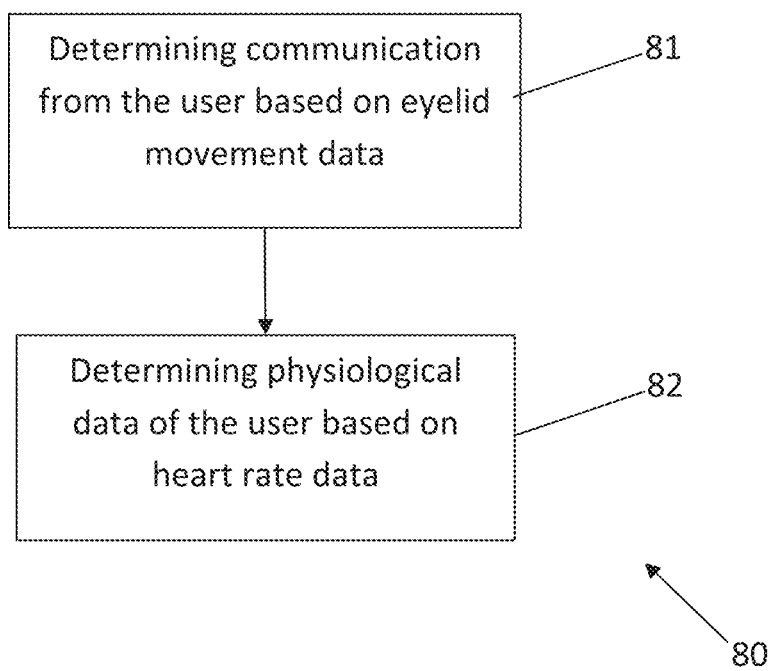
FIG. 8 is a flowchart showing an algorithm in accordance with an example embodiment.

FIG. 8 is a flowchart of an algorithm, indicated generally by the reference numeral 80, in accordance with an example embodiment. At operation 81, the determined eyelid movement data may be used for determining communication from the user. At operation 82, the determined heart rate data may be used for determining physiological data of the user (e.g. stress level and/or other physiological conditions which may be estimated using the heart rate data).

In an example embodiment, the eyewear device 11 (as shown in the system 10 and the first electrical circuit 30 with reference to FIGS. 1 and 3) may be used as a communication interface for persons with certain disorders (e.g. a person with ALS). For example, at operation 81, information which the person wishes to communicate may be mapped based on eyelid movement data, including one or more of the duration of one or more eye blinks, the number of eye blinks, the frequency of eye blinks, or the extent to which the eye(s) is(are) closed (e.g. the amplitude of the first increase 51 or 61). The current and/or voltage measurements (as shown in plots 50 and 60) may be analysed in a frequency domain (e.g. using a Fourier transformation, Fast Fourier transformation, etc.) for estimation of heart rate data and eyelid movement data.

Figure 9:
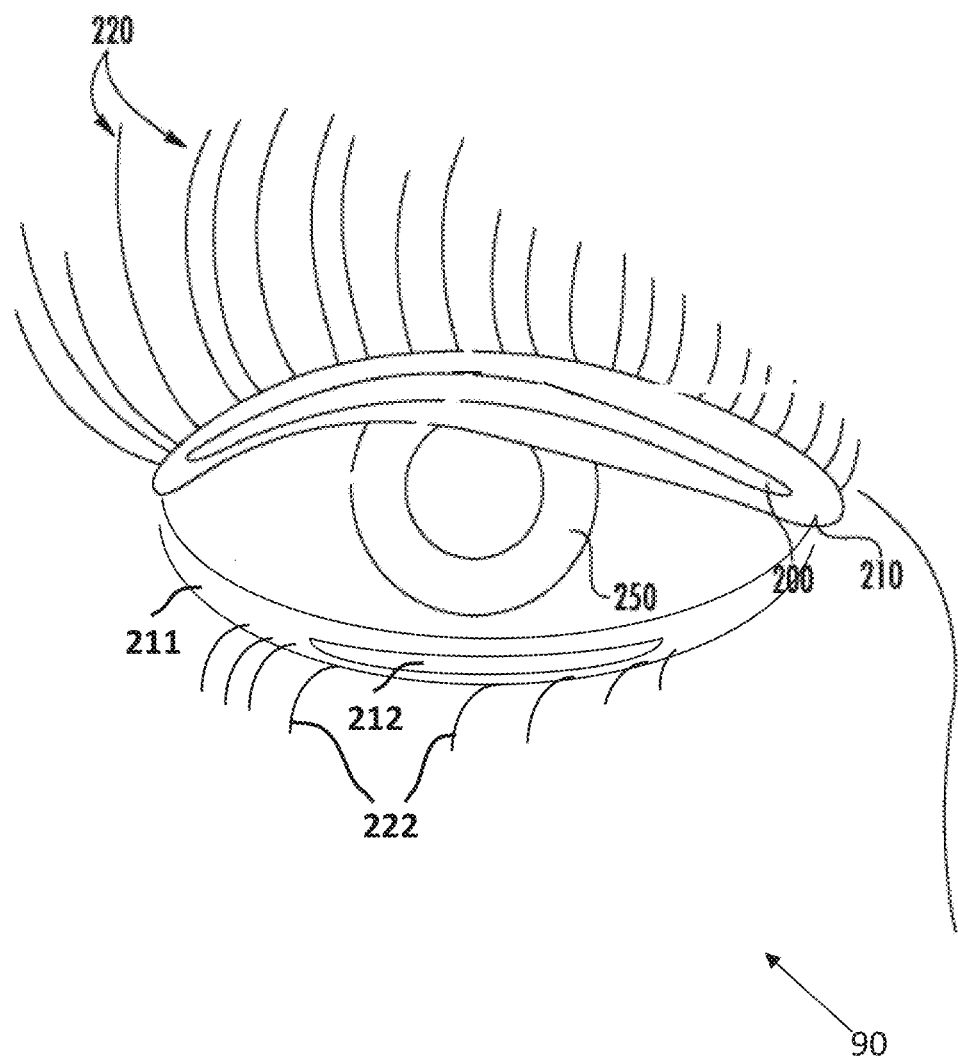
FIG. 9 is an example illustration of a system in accordance with an example embodiment.

FIG. 9 is an example illustration of a system, indicated generally by the reference numeral 90, in accordance with an example embodiment. System 90 shows an eye of a user comprising a first eyelid 210 (e.g. upper eyelid), a second eyelid 211 (e.g. lower eyelid), a lens 250, eyelashes 220, an example first eyelid electrode 200 and an example second eyelid electrode 212. As shown in system 90, the first eyelid electrode 200 may be provided at the first eyelid 210, and the second eyelid electrode 212 may be provided at the second eyelid 211, for example, using conductive make-up e.g. conductive ink, conductive powder, or the like. Alternatively, or in addition, the first eyelid electrode 200 may be provided on one or more of the upper eyelashes 220 and/or the second eyelid electrode may be provided on one or more of the lower eyelashes 222. For example, eyelashes 220 and/or 222 may be fake eyelashes attached to the eyelid, or conductive ink or mascara provided on the user's eyelashes.

Figure 10:
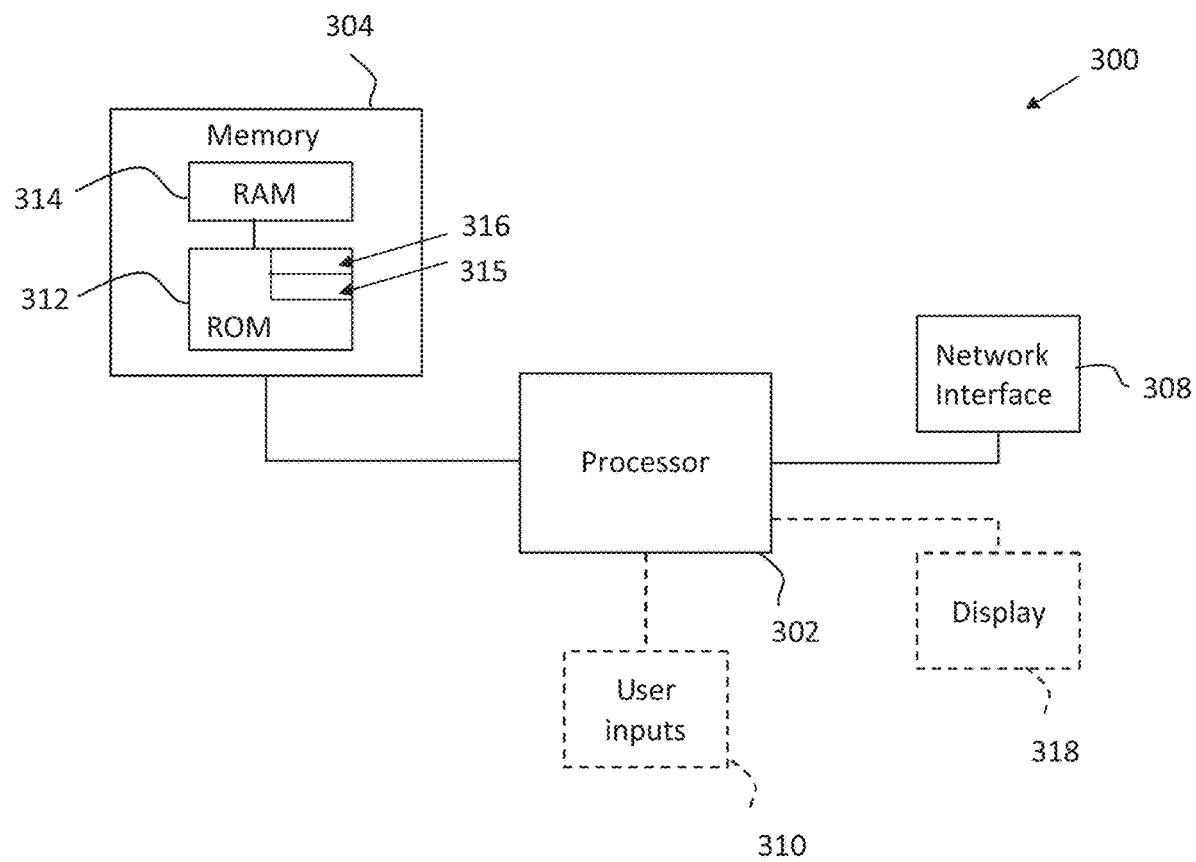
FIG. 10 is a block diagram of components of a system in accordance with an example embodiment.

For completeness, FIG. 10 is a schematic diagram of components of one or more of the example embodiments described previously, which hereafter are referred to generically as a processing system 300. The processing system 300 may, for example, be the apparatus referred to in the claims below.

The processing system 300 may have a processor 302, a memory 304 coupled to the processor and comprised of a RAM 314 and a ROM 312, and, optionally, a user input 310 and a display 318. The processing system 300 may comprise one or more network/apparatus interfaces 308 for connection to a network/apparatus, e.g. a modem which may be wired or wireless. The interface 308 may also operate as a connection to other apparatus such as device/apparatus which is not network side apparatus. Thus, direct connection between devices/apparatus without network participation is possible.

The processor 302 is connected to each of the other components in order to control operation thereof.

The memory 304 may comprise a non-volatile memory, such as a hard disk drive (HDD) or a solid state drive (SSD). The ROM 312 of the memory 304 stores, amongst other things, an operating system 315 and may store software applications 316. The RAM 314 of the memory 304 is used by the processor 302 for the temporary storage of data. The operating system 315 may contain code which, when executed by the processor implements aspects of the algorithms 40, 70, and 80 described above. Note that in the case of small device/apparatus the memory can be most suitable for small size usage i.e. not always a hard disk drive (HDD) or a solid state drive (SSD) is used.

The processor 302 may take any suitable form. For instance, it may be a microcontroller, a plurality of microcontrollers, a processor, or a plurality of processors.

The processing system 300 may be a standalone computer, a server, a console, or a network thereof. The processing system 300 and needed structural parts may be all inside device/apparatus such as IoT device/apparatus i.e. embedded to very small size hi some example embodiments, the processing system 300 may also be associated with external software applications. These may be applications stored on a remote server device/apparatus and may run partly or exclusively on the remote server device/apparatus. These applications may be termed cloud-hosted applications. The processing system 300 may be in communication with the remote server device/apparatus in order to utilize the software application stored there.

Figure 11A:
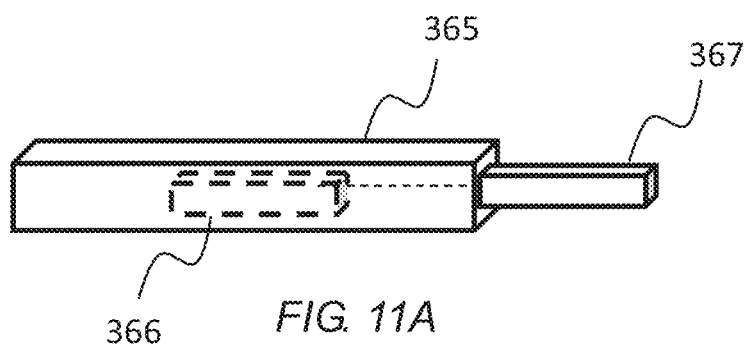
FIGS. 11A and 11B show tangible media, respectively a removable non-volatile memory unit and a Compact Disc (CD) storing computer-readable code which when run by a computer perform operations according to example embodiments.
Figure 11B:
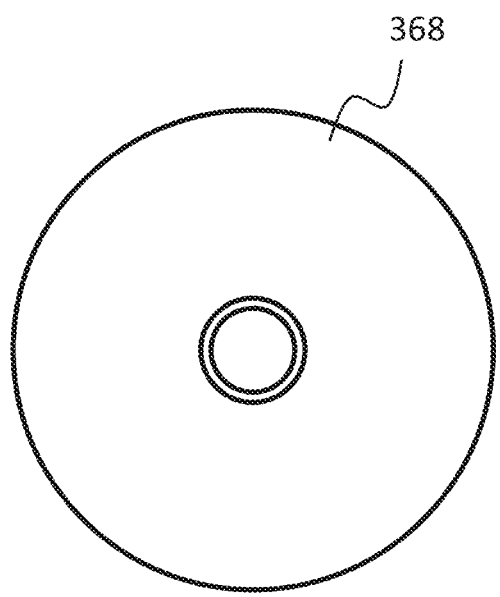

FIGS. 11A and 11B show tangible media, respectively a removable memory unit 365 and a compact disc (CD) 368, storing computer-readable code which when run by a computer may perform methods according to example embodiments described above. The removable memory unit 365 may be a memory stick, e.g. a USB memory stick, having internal memory 366 storing the computer-readable code. The internal memory 366 may be accessed by a computer system via a connector 367. The CD 368 may be a CD-ROM or a DVD or similar. Other forms of tangible storage media may be used. Tangible media can be any device/apparatus capable of storing data/information which data/information can be exchanged between devices/apparatus/network.

Embodiments of the present invention may be implemented in software, hardware, application logic or a combination of software, hardware and application logic. The software, application logic and/or hardware may reside on memory, or any computer media. In an example embodiment, the application logic, software or an instruction set is maintained on any one of various conventional computer-readable media. In the context of this document, a "memory" or "computer-readable medium" may be any non-transitory media or means that can contain, store, communicate, propagate or transport the instructions for use by or in connection with an instruction execution system, apparatus, or device, such as a computer.

Reference to, where relevant, "computer-readable medium", "computer program product", "tangibly embodied computer program" etc., or a "processor" or "processing circuitry" etc. should be understood to encompass not only computers having differing architectures such as single/multi-processor architectures and sequencers/parallel architectures, but also specialised circuits such as field programmable gate arrays FPGA, application specify circuits ASIC, signal processing devices/apparatus and other devices/apparatus. References to computer program, instructions, code etc. should be understood to express software for a programmable processor firmware such as the programmable content of a hardware device/apparatus as instructions for a processor or configured or configuration settings for a fixed function device/apparatus, gate array, programmable logic device/apparatus, etc.

If desired, the different functions discussed herein may be performed in a different order and/or concurrently with each other. Furthermore, if desired, one or more of the above-described functions may be optional or may be combined. Similarly, it will also be appreciated that the flow diagrams of FIGS. 4, 7 and 8 are examples only and that various operations depicted therein may be omitted, reordered and/or combined.

It will be appreciated that the above described example embodiments are purely illustrative and are not limiting on the scope of the invention. Other variations and modifications will be apparent to persons skilled in the art upon reading the present specification.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

Although various aspects of the invention are set out in the independent claims, other aspects of the invention comprise other combinations of features from the described example embodiments and/or the dependent claims with the features of the independent claims, and not solely the combinations explicitly set out in the claims.

It is also noted herein that while the above describes various examples, these descriptions should not be viewed in a limiting sense. Rather, there are several variations and modifications which may be made without departing from the scope of the present invention as defined in the appended claims.

What is claimed is:

1. An apparatus, comprising:
   an eyewear device;
   a first device electrode and a second device electrode on the eyewear device;
   a first eyelid electrode configured to be positioned on a first eyelid of a user and a second eyelid electrode configured to be positioned on a second eyelid of the user;
   an electrical circuit formed from the first device electrode, the first eyelid electrode, the second eyelid electrode, and the second device electrode;
   at least one processor;
   a display coupled to the at least one processor configured to communicate with the user; and
   at least one non-transitory memory storing instructions that, when executed with the at least one processor, cause the apparatus to:
   apply an electrical signal to the electrical circuit, the electrical signal passing through the first device electrode to the first eyelid electrode, from the first eyelid electrode to the second eyelid electrode through an eyeball electrical path, from the second eyelid electrode to the second device electrode, and from the second device electrode to the first device electrode;
   determine at least one of a current or voltage measurement of the electrical circuit; and
   use one or more variants of an algorithm stored in the at least one non-transitory memory, the one or more variants of the algorithm operating to determine movement data based on one or more variations in the at least one of the current or voltage measurement,
   wherein:
   the at least one of the current or voltage measurement is used to determine heart rate data and eyelid movement data for the user,
   the eyelid movement data being determined from a first increase in the at least one of the current or voltage measurement, and
   the heart rate data being determined by a second increase in the at least one of the current or voltage measurement,
   wherein the eyelid movement data and the heart rate data are distinguished based on differences in at least one of frequency, duration, or amplitude of the first increase and the second increase, and
   wherein the determined eyelid movement data and the determined heart rate data are used to assist communication with the user through a network interface.

2. The apparatus as claimed in claim 1, wherein the instructions, when executed with the at least one processor, cause the apparatus at least to further determine the heart rate data and the eyelid movement data for the user based on the one or more variations in the at least one of the current or voltage measurement of the electrical circuit.

3. The apparatus as claimed in claim 1,
   wherein the first device electrode is configured to form a first capacitor with the first eyelid electrode, wherein the first capacitor has a first capacitance;
   wherein the second device electrode is configured to form a second capacitor with the second eyelid electrode, wherein the second capacitor has a second capacitance; and
   wherein the instructions, when executed with the at least one processor, further cause the apparatus to determine the at least one of the current or voltage measurement of the electrical circuit, wherein a current or voltage is generated in the electrical circuit in response to the applied electrical signal; and
   determine the heart rate data and the eyelid movement data for the user based on the one or more variations in the at least one of the current or voltage measurement.

4. The apparatus as claimed in claim 3, wherein the instructions, when executed with the at least one processor, cause the apparatus to determine the eyelid movement data by determining the first increase in the at least one of the current or voltage measurement, wherein the first increase is caused by an increase in at least one of the first capacitance or the second capacitance.

5. The apparatus as claimed in claim 4, wherein a duration of the first increase is used for determining a duration of a first eyelid movement.

6. The apparatus as claimed in claim 5, wherein the increase in at least one of the first capacitance or the second capacitance is based on a decrease in at least one of a first distance between the first device electrode and the first eyelid electrode or a second distance between the second device electrode and the second eyelid electrode, wherein the decrease is caused by the first eyelid movement.

7. The apparatus as claimed in claim 4, wherein the instructions, when executed with the at least one processor, cause the apparatus to determine heart rate by determining the second increase in a first current or voltage measurement;
wherein the second increase is used for determining an increase in a first impedance of the eyeball electrical path due to changes in blood concentration during a plurality of heartbeats,
wherein a frequency of the increase in the first impedance is used for determining the heart rate data, and
wherein the first impedance is formed from an eyeball resistance and eyeball capacitance of the eyeball of the user.

8. The apparatus as claimed in claim 2, wherein the first increase has a higher amplitude relative to the second increase and the first increase has a lower frequency relative to the second increase.

9. The apparatus as claimed in claim 1, wherein the determined eyelid movement data is used for determining a communication from the user, and wherein the heart rate data is used for determining physiological data of the user.

10. A method, comprising:
applying an electrical signal to an electrical circuit, wherein the electrical is circuit is formed between:
a first device electrode and a first eyelid electrode, wherein:
the first device electrode is configured to be provided on a first portion of an eyewear device; the first eyelid electrode is configured to be provided on a first eyelid of a user; the first device electrode forms a first capacitor with the first eyelid electrode;
and the first capacitor has a first capacitance;
an eyeball electrical path between the first eyelid electrode and a second eyelid electrode;
the second eyelid electrode and a second device electrode, wherein:
the second device electrode is configured to be provided on a second portion of the eyewear device; the second eyelid electrode is configured to be provided on a second eyelid of the user; the second device electrode forms a second capacitor with the second eyelid electrode; and the second capacitor has a second capacitance; and
the second device electrode and the first device electrode; and
determining current or voltage measurements of the electrical circuit, wherein the current or voltage measurements are used to determine heart rate data and eyelid movement data for the user; and
using one or more variants of an algorithm, the one or more variants of the algorithm operating to determine movement data based on one or more variations in the current or voltage measurements,
wherein the current or voltage measurements are used to determine the heart rate data and the eyelid movement data for a user,
the eyelid movement data being determined from a first increase in the current or voltage measurements, and the heart rate data being determined by a second increase in the current or voltage measurements,
wherein the eyelid movement data and the heart rate data are distinguished based on differences in at least one of frequency, duration, or amplitude of the first increase and the second increase, and
wherein the determined eyelid movement data and the determined heart rate data are used to assist communication with the user through a network interface via a display.

11. The method as claimed in claim 10, further comprising determining the heart rate data and the eyelid movement data for the user based on the one or more variations in the current or voltage measurements of the electrical circuit.

12. The apparatus as claimed in claim 11, wherein determining the heart rate data and the eyelid movement data is configured to determine eyelid movement data by determining the first increase in the current or voltage measurements, wherein the first increase is caused by an increase in at least one of the first capacitance and the second capacitance.

13. The apparatus as claimed in claim 12, wherein a duration of the first increase is used for determining a duration of a first eyelid movement.

14. The apparatus as claimed in claim 12, wherein the increase in at least one of the first capacitance and the second capacitance is based on a decrease in at least one of a first distance between the first device electrode and the first eyelid electrode, and a second distance between the second device electrode and the second eyelid electrode, wherein the decrease is caused by the first eyelid movement.

15. A non-transitory computer readable medium comprising program instructions stored thereon for performing at least the following:
applying an electrical signal to an electrical circuit formed between a first device electrode and a first eyelid electrode, an eyeball electrical path between the first eyelid electrode and a second eyelid electrode, the second eyelid electrode and a second device electrode, and the second device electrode and the first device electrode;
wherein the first device electrode is configured to be provided on a first portion of an eyewear device, the second device electrode is configured to be provided on a second portion of the eyewear device, the first eyelid electrode is configured to be provided on a first eyelid of a user, and the second eyelid electrode is configured to be provided on a second eyelid of the user;
wherein, the first device electrode is configured to form a first capacitor with the first eyelid electrode, wherein the first capacitor has a first capacitance; and wherein the second device electrode is configured to form a second capacitor with the second eyelid electrode provided on the second eyelid of the user, wherein the second capacitor has a second capacitance;
determining at least one of current or voltage measurements of the electrical circuit, wherein the at least one of the current or voltage measurements is generated in the electrical circuit in response to the applied electrical signal; and
using one or more variants of an algorithm, the one or more variants of the algorithm operating to determine movement data based on one or more variations in the at least one of the current or voltage measurements, wherein the at least one of the current or voltage measurements is used to determine heart rate data and eyelid movement data for a user, the eyelid movement data being determined from a first increase in the at least one of the current or voltage measurements, and the heart rate data being determined by a second increase in the at least one of the current or voltage measurements, wherein the eyelid movement data and the heart rate data are distinguished based on differences in at least one of frequency, duration, or amplitude of the first increase and the second increase, and wherein the determined eyelid movement data and the determined heart rate data are used to assist communication with the user through a network interface via a display.

16. The non-transitory computer readable medium as claimed in claim 15, comprising program instructions stored thereon for further performing at least the following: determining the heart rate data and the eyelid movement data for the user based the one or more variations in the at least one of the current or voltage measurements.

* * * * *